United States Patent [19]

Buelna

[11] Patent Number: 5,080,660
[45] Date of Patent: Jan. 14, 1992

[54] ELECTROSURGICAL ELECTRODE

[75] Inventor: Terrence J. Buelna, Rancho Santa Margarita, Calif.

[73] Assignee: Applied Urology, Inc., Laguna Hills, Calif.

[21] Appl. No.: 522,254

[22] Filed: May 11, 1990

[51] Int. Cl.⁵ .............................................. A61B 17/39
[52] U.S. Cl. ........................................ 606/45; 606/46; 606/48; 606/49; 606/50
[58] Field of Search ........................ 606/41, 42, 45–50

[56] References Cited

U.S. PATENT DOCUMENTS

| | | | |
|---|---|---|---|
| 1,814,791 | 7/1931 | Ende | 606/50 |
| 3,799,168 | 3/1974 | Peters . | |
| 3,987,795 | 10/1976 | Morrison | 606/48 |
| 4,161,950 | 7/1979 | Doss . | |
| 4,314,559 | 2/1982 | Allen . | |
| 4,333,467 | 6/1982 | Domicone . | |
| 4,481,057 | 11/1984 | Beard . | |
| 4,534,347 | 8/1985 | Taylor . | |
| 4,545,375 | 10/1985 | Cline . | |
| 4,589,411 | 5/1986 | Friedman . | |
| 4,622,966 | 11/1986 | Beard . | |
| 4,657,016 | 4/1987 | Garito . | |
| 4,785,807 | 11/1988 | Blanch . | |
| 4,976,711 | 12/1990 | Parims et al. | 606/48 |

Primary Examiner—Lee S. Cohen
Attorney, Agent, or Firm—Richard L. Myers

[57] ABSTRACT

In accordance with an embodiment of the present invention an improvement is set forth in an electrosurgical electrode having a conductor from which a radio frequency electrical signal is generated, which signal sparks to and performs a surgical procedure upon the tissue adjacent the conductor and is received by a receiver. The improvement comprises a dielectric sheath surrounding the conductor in the region where the surgical procedure is being performed, the sheath having a slit extending longitudinally along it in the region exposing only a portion of the lateral surface of the conductor.

21 Claims, 5 Drawing Sheets

ELECTROSURGICAL ELECTRODE

TECHNICAL FIELD

The invention relates to electrosurgical cutting and coagulating and more particularly to improved electrosurgical cutting and coagulating electrodes.

BACKGROUND OF THE INVENTION

In monopolar electrosurgical cutting a current is allowed to pass from an active cutting electrode through a patient's tissue and into a grounding pad or cable. The current cuts tissue at the active cutting electrode, the cutting rate being dependant on current density through the tissue in that area. At low current density heat is generated but no cut is achieved. At high current density fast cutting occurs.

In bipolar electrosurgical cutting the current passes from the active cutting electrode through the patient's tissue to a return electrode which is located in, or is in contact with, the patient's tissue a short distance away from the cutting electrode. The cutting and return electrodes are generally carried by a single instrument.

Current density depends on the applied electrical power (measured in watts) which can be controlled utilizing an adjustment present on a conventional generator designed for this purpose. The current density also depends on the series impedance of the overall circuit Series impedance is equivalent to the sum total of the resistance to the current throughout the circuit. It is affected by the material and the design of the active electrode, by the patient, by the type of tissue to be cut, and by the condition of contact established between the patient and (when a monopolar electrode is utilized) the grounding pad as well as by the location of the grounding pad relative to the cutting site. During surgery, the generator setting is usually adjusted to compensate for this variability and to reflect the surgeon's preference. Generators used in this type of surgery have a wide range of power outputs to accommodate a variety of procedures and devices.

The objective in electrosurgical cutting is to heat the tissues cells so rapidly that they explode into steam leaving a cavity in the cell matrix. The heat is meant to be dissipated in the steam rather than be conducted through the tissue to thereby dry cut adjacent cells. When the electrode is moved and fresh tissue is contacted new cells are exploded and the incision is made. Such electrosurgical cutting involves the sparking of the current to the tissue. The current utilized is in the radio frequency range and operates by the radio frequency current jumping across an air gap to the tissue. This is known as sparking.

An explanation of electrosurgical cutting theory can be found in the FORCE 1 Instruction Manual published by Valleylab of Boulder, Colo. on Mar. 1, 1986. The entire text of the FORCE 1 Instruction Manual is incorporated herein by reference.

An advantage touted for electrosurgical cutting is that adjacent tissue is not supposed to become overly heated and thereby desiccated and damaged. Thus, what one desires is a clean cut without damage to adjacent tissue. Unfortunately, current electrosurgical cutting electrodes are of a construction such that sufficient heating of adjacent tissue does occur it is somewhat damaged and desiccated.

Electrosurgical fulguration/coagulation operates similarly but at different power levels and using shorter bursts of higher peak voltages as discussed on page 5 of the FORCE 1 publication.

The present invention is directed to overcoming one or more of the problems as set forth above.

DISCLOSURE OF INVENTION

In accordance with an embodiment of the present invention an improvement is set forth in an electrosurgical apparatus having an electrode in the form of an electrical conductor. Radio frequency electrical signal is passed into the conductor and generates a spark which cuts adjacent body tissue of a patient. In monopolar electrodes, the signal is introduced into the active electrode and received by a receiver (grounding pad) which may be removed from the tissue being. In bipolar electrodes, the receiver is adjacent to the active electrode. In either case, the improvement comprises a dielectric sheath surrounding the conductor in the region of the surgical procedure, the sheath having a slit extending along the electrode exposing only a portion of the lateral surface of the conductor.

Utilizing an electrosurgical cutter and/or fulgurator/coagulator having a dielectric sheath as set forth above leads to the sparking being confined to the region of the slit. The dielectric sheath serves to protect adjacent tissue from being heated and desiccated. Yet, the conductor can be as thick as conventional conductors utilized in electrosurgical cutters in order to maintain strength and integrity. As a result, a very clean cut can be made without damage to surrounding tissues, or to the cutting electrode. Or, fulguration/coagulation can be controllably carried cut. Furthermore, cutting can only occur in the direction defined by the slit whereby improved orientation of the cutting is accomplished. The chances of accidentally cutting in an undesired direction is reduced as slit alignment may be such that accidental cutting does not occur in that direction.

BRIEF DESCRIPTION OF THE DRAWINGS

The invention will be better understood by reference to the figures of the drawings wherein like numbers denote like parts throughout and wherein.

BEST MODE FOR CARRYING OUT INVENTION

The present invention is directed to an improvement in a surgical electrode 10,110,210, 10,410,510,610 of any convenient configuration. Embodiments of such electrodes are shown in FIGS. 1–10. The particular electrosurgical electrodes shown in FIGS. 3–10 are adapted for operations in the genitourinary tract, more particularly for prostate operations. However, electrodes in accordance with the invention can be used in any surgical procedure in which electrosurgical electrodes are suitable. In such instances other geometries can be utilized, as appropriate. An electrosurgical electrode in accordance with the present invention can be utilized with conventional commercial resectoscopes, radio frequency generators and grounding pads.

When the term surgical procedure is used herein it is used in a broad sense so as to include procedures in which cutting does or does not occur. For example, the electrodes of the invention can be used to form incisions and/or for fulguration/coagulation, with or without accompanying cutting. In either instance the procedure is considered surgical.

Figure 3:
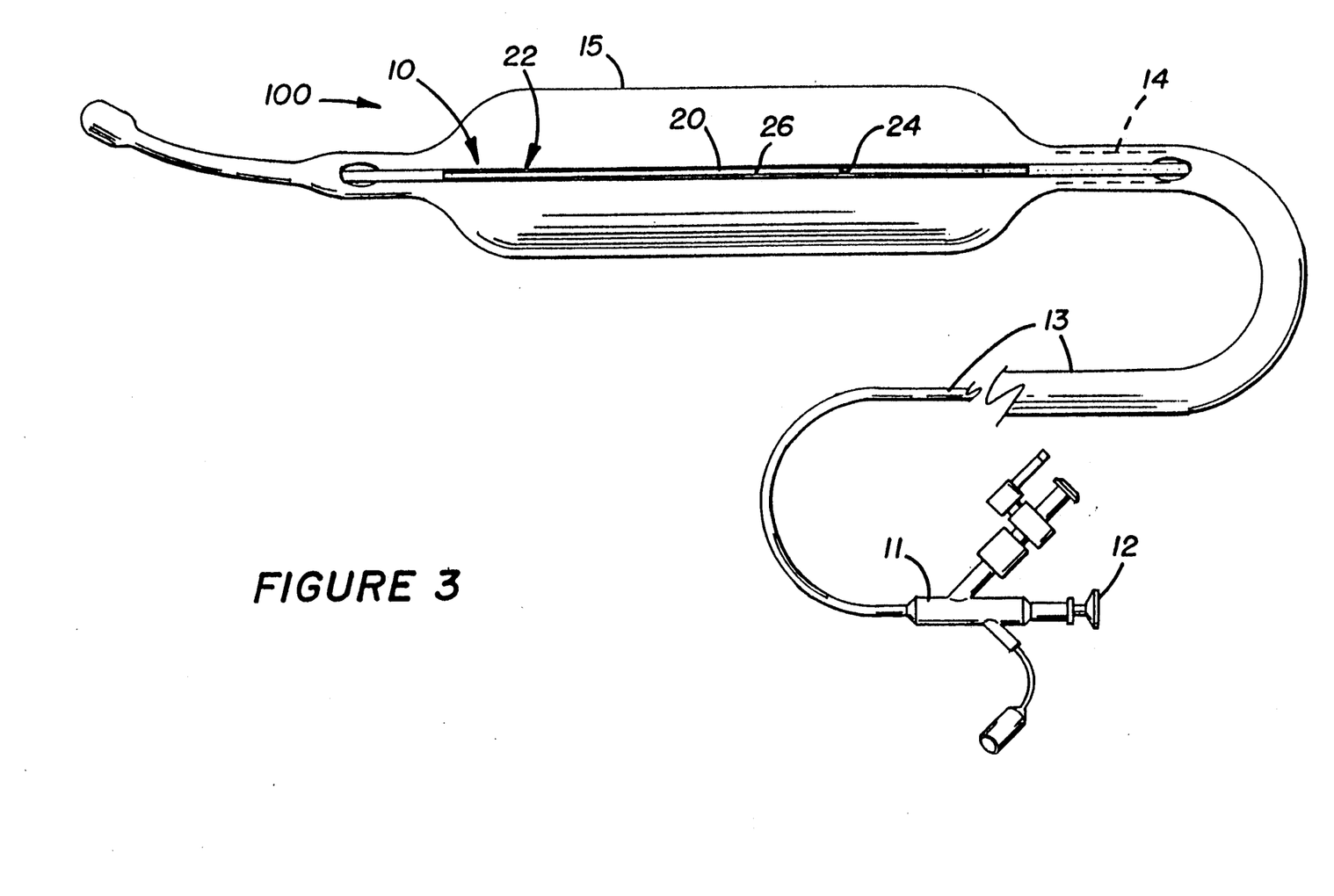
FIG. 3 illustrates, in partial isometric view, one embodiment of an electrosurgical cutting assembly including an improvement in accordance with an embodiment of the present invention.

The cutting assembly 100 of FIG. 3 includes means for dilating a body vessel or conduit, such as a ureter or urethra, to treat a blockage or other obstruction. The main components of the embodiment of the nature shown in FIG. 3 are an adapter 11 that defines the proximal end 12 of the assembly and provides a site for various ports to the assembly; a catheter body 13 having a triple lumen 14; a longitudinally extending inflatable balloon or bladder member 15; and an electrosurgical cutter electrode 10. One of the three passageways of the triple lumen 14 serves for inflation/deflation, a second serves as a drainage/infusion/guide wire passageway and a third carries the electrosurgical cutter electrode 10. The apparatus shown in FIG. 3 is more completely described in copending application Ser. No. 07/298,477 filed Jan. 18, 1989 now abandoned, which is incorporated herein in its entirety by reference thereto. The electrosurgical cutter electrode 10 is in the nature of a wire 20 which extends generally parallel to the longitudinal inflatable bladder 15.

In use, the bladder 15 is inserted longitudinally into a body conduit to the position where a surgical cut is required. The bladder 15 is then inflated (an inextensible bladder is generally used) with radio frequency current being passed through the wire 20. This leads to the wire being moved outwardly and incising adjacent tissue in that direction. A sheath 22, with a slit 24 in it and facing away from the bladder 15, surrounds the wire 20. The improvement of the present invention is particularly useful with the apparatus of FIG. 3.

Figure 4:
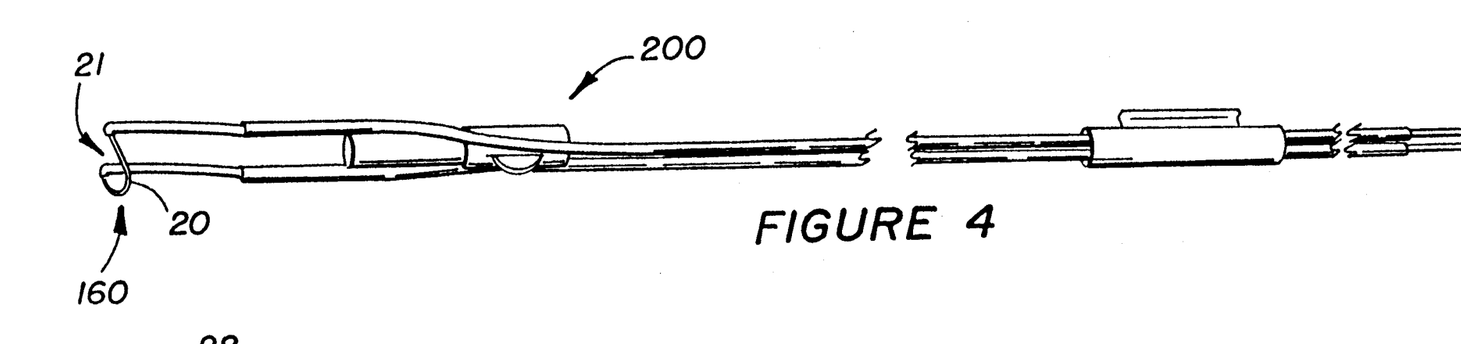
FIG. 4 illustrates, in isometric view, another embodiment of an electrosurgical cutting assembly including an improvement in accordance with an embodiment of the present invention.

FIG. 4 shows an alternative electrosurgical cutting assembly 200 which can be used for transurethral resection of the prostate. The electrosurgical cutting assembly 200 of FIG. 4 includes a cutter electrode 110 which includes a wire 20 in shape of a cutting loop 21. An electrosurgical cutting assembly 200 of this nature is conventionally passed through a resectoscope which is inserted into the urethra. A radio frequency signal is then applied to the cutter electrode 110 whereby the signal is passed from the wire 20 through the tissue to a grounding pad (not illustrated) in contact with the patient's body at a position removed from the wire 20. The electrosurgical cutter electrode 110 can be moved longitudinally toward the surgeon to cut away or resection the prostate.

Figure 5:
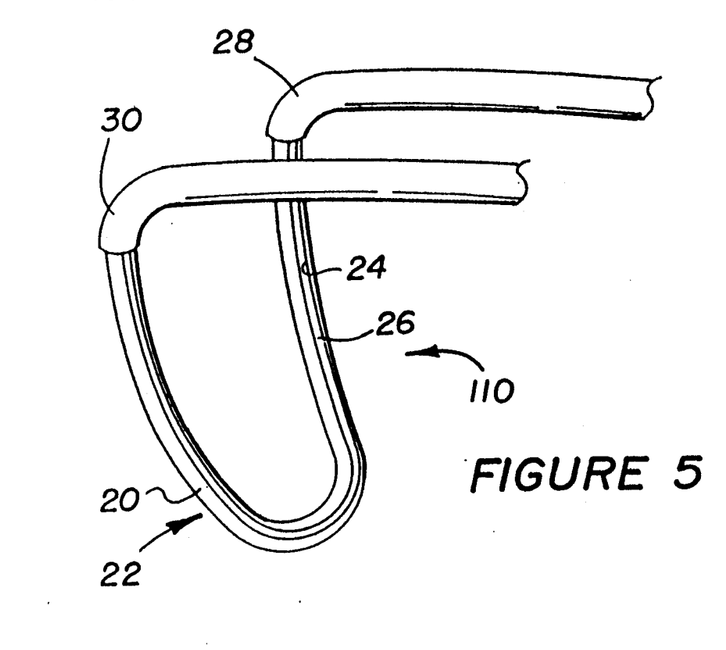
FIG. 5 illustrates, in partial isometric view, an embodiment in accordance with the present invention useful for transurethral resection of the prostate.

FIG. 5 shows the distal end of the electrosurgical cutter electrode 110 of FIG. 4 in more detail. A dielectric sheath 22 surrounds the wire 20 and has a slit 24 in it facing proximally (toward the surgeon).

Figure 6:
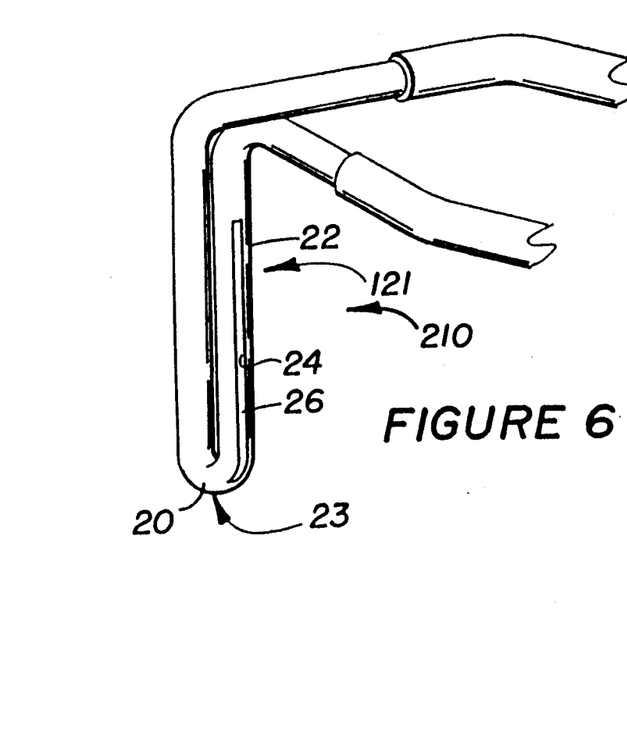
FIG. 6 illustrates, in partial isometric view, an embodiment in accordance with the invention useful for transurethral incision of the prostrate.

FIG. 6 shows a cutter electrode 210 with the wire 20 having a closed loop 121 in it rather than an open loop 21 whereby it can be used to cut a thin line into the prostate or other organ as the overall electrosurgical cutting assembly 200 is moved longitudinally. Note the presence of the sheath 22 with the slit 24 facing proximally and located adjacent a bend 23 in the closed loop 121. Such a procedure is known as transurethral incision of the prostate when used in prostate operations.

Figure 7:
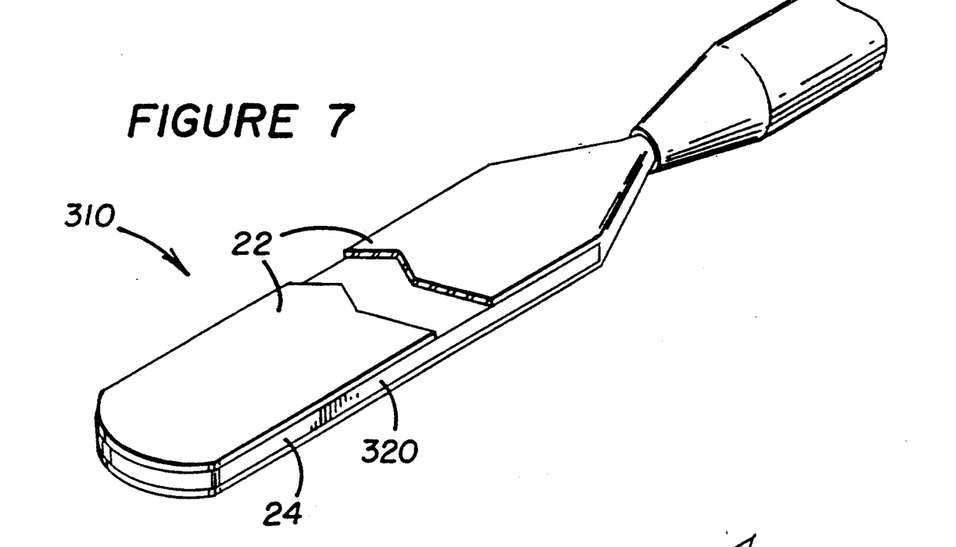
FIG. 7 illustrates, in partial isometric view, still another embodiment in accordance with the invention.

FIG. 7 illustrates a Bovie blade type of monopolar cutting electrode 310 covered by the sheath 22 which may be a surface coating and with a slit 24 exposing a portion of the surface of the underlying conductor 320 which is flat in shape. As with other embodiments of the invention, cutting (or fulguration/coagulation) is only in the direction of the slit 24.

Figure 8:
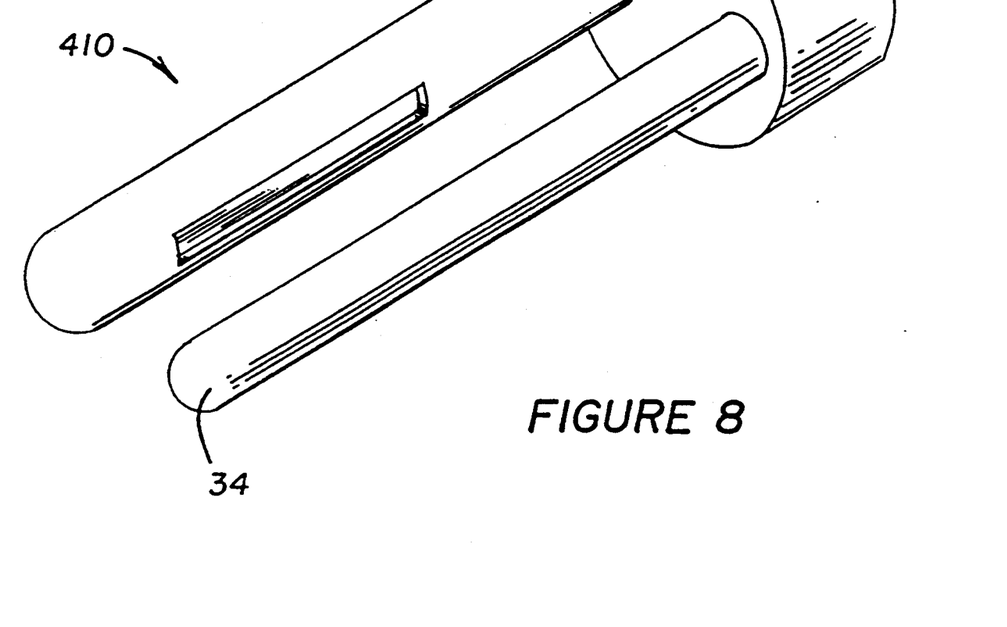
FIG. 8 illustrates, in partial isometric view, a bipolar structure in accordance with yet another embodiment of the invention.

FIG. 8 illustrates a bipolar electrosurgical cutter electrode 410 along with a return electrode 34 which can be fully exposed. The cutter electrode 410 is covered by the sheath 22 with a slit 24 exposing a portion of the lateral surface 26 of the wire 20. Cutting is in the direction of the slit 24 and the return electrode 34 serves to complete the circuit.

Figure 9:
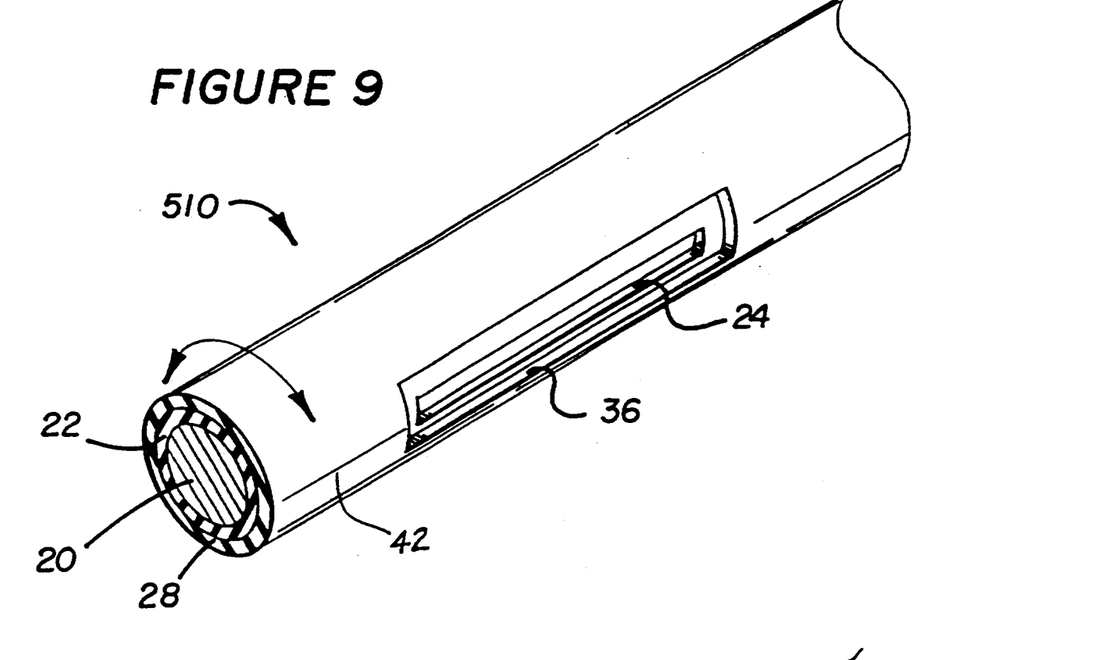
FIG. 9 illustrates, in a view similar to FIG. 1, an embodiment with one type of controllable effective sparking aperture.

FIG. 9 illustrates an electrosurgical cutter electrode 510 wherein a sleeve structure 42 is located concentrically about the sheath 22 and has a window 36 through it. In FIG. 9 the window 36 exposes only a portion of the slit 24 whereby the resulting cutting aperture 40 is narrower than the slit 24. The sleeve structure 42 can be rotated about, and generally slid longitudinally along, the sheath 22 to control the width of the effective cutting aperture 40 (and usually its length, as well). Thus, a relatively narrow aperture 40 can be used for cutting and a wider effective aperture 40 for fulguration/coagulation.

Figure 10:
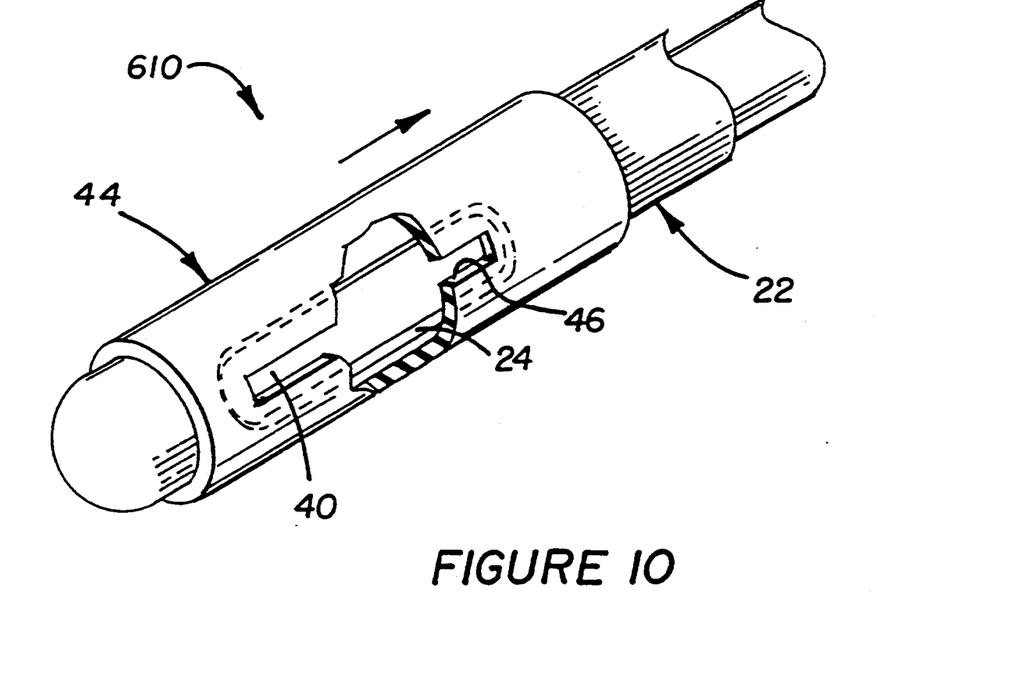
FIG. 10 illustrates, in a view similar to FIG. 1, an embodiment with a second type of controllable effective sparking aperture.

FIG. 10 illustrates an electrosurgical cutter electrode 610 wherein a sleeve structure 44 has a relatively narrow window 46 covering a wide slit 24 in the sheath 22, the window 46 being of a size selected to provide an effective cutting aperture 40. The sleeve structure 44 is longitudinally moveable along the sheath 22 sufficiently to entirely expose the wide slit 24 for faster fulguration/coagulation.

Figure 1:
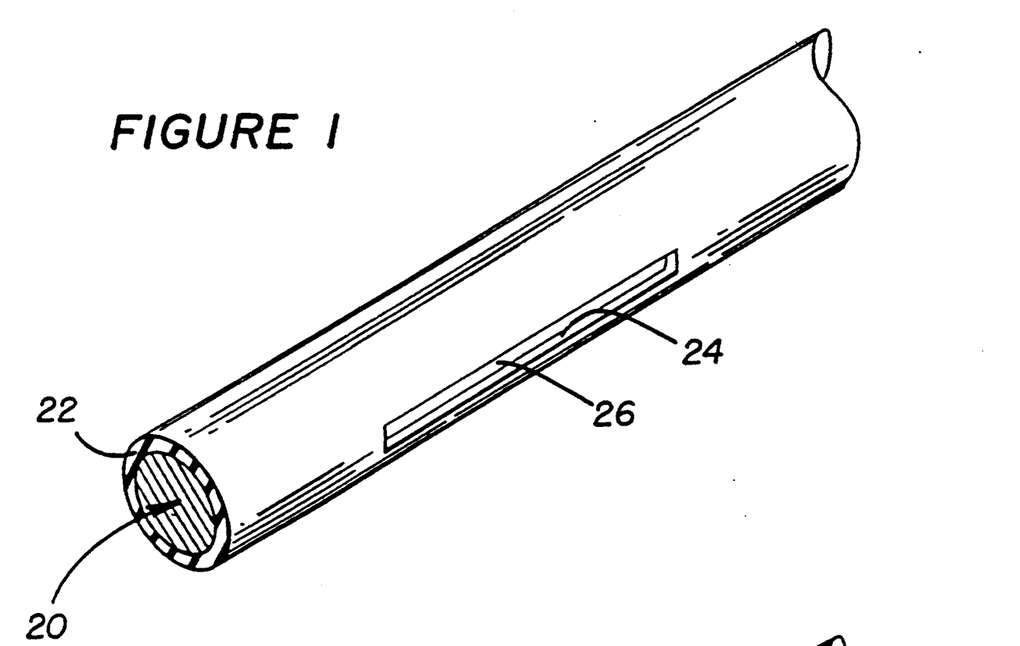
FIG. 1 illustrates, in partial isometric view, a detail of an improvement in accordance with an embodiment of the present invention.
Figure 2:
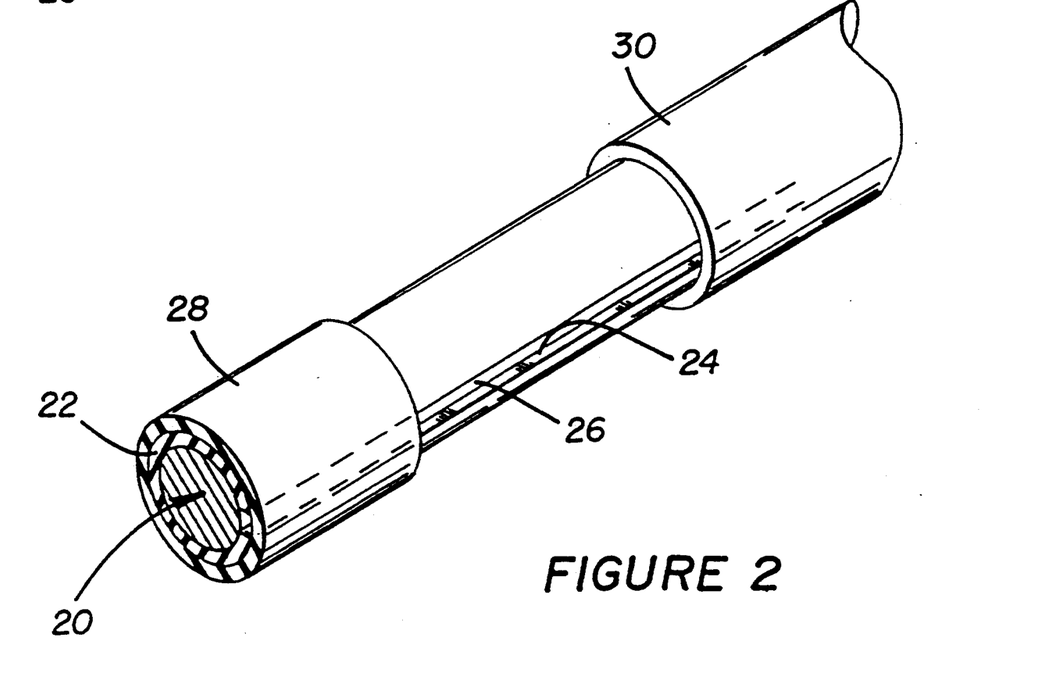
FIG. 2 illustrates, in partial isometric view, a detail of an improvement in accordance with another embodiment of the present invention.

FIGS. 1 and 2 illustrate, in enlarged view, alternative embodiments of the improvement of the present invention.

FIG. 1 illustrates an embodiment wherein a dielectric sheath 22 surrounds the wire 20 in the region where it performs the cutting and wherein the sheath 22 has a slit 24 which extends along it in the region where it performs the cutting, the slit 24 exposing only a portion of the lateral surface 26 of the wire 20. Generally, the slit 24 extends longitudinally along the sheath 22. The sheath 22 can be slidably placed about the wire 20 to allow adjustable placement of the slit 24. In the embodiment shown in FIG. 1 the slit 24 is in the sheath 22 only in the region where the wire 20 is to perform the cutting.

In the embodiment of FIG. 2, the slit 24 runs along the sheath 22 and exposes the wire 20 over a longer region than that where the tissue is to be cut. For example, the slit 24 can run substantially the entire length of the wire 20. However, in this embodiment dielectric sleeve s 28 and 30 fit over the sheath 22 whereby the only region of the wire 20 which is exposed through the slit 24 is that region where the wire 20 performs the cutting. Reference to FIGS. 5 and 6 will make clear the placement of the sleeves 28 and 30. The sleeves 28 and 30 can be slidably disposed about the sheath 22, whereby the length and positioning of the region of the wire 20 can be adjusted by the surgeon.

It should be noted that while the wires 20 are illustrated as being circular in cross-section the shape of the wires 20 is a matter of design choice and the invention is not so limited.

The material used for the wire 20 can be any conductive material, for example, it can be made of any of the materials currently used for electrosurgical cutting wires such as stainless steel or tungsten.

The dielectric sheath 22 may be in the nature of a surface coating bonded or deposited onto the wire 20. Alternatively, it may be in the nature of a non-attached sheath which slidingly or bindingly fits about the wire 20. The sheath 22 can be made of any convenient material which has dielectric properties such that the wire 20 is prevented from sparking to and thereby cutting adjacent tissue other than through the slit 24. Any of a number of polymeric materials can be used for the material of the sheath 22. For example, Teflon (trademark of Du Pont), is one such material. Teflon has the advantages of high lubricity whereby it does not have a tendency to stick to tissue and of thermal stability.

The electrosurgical cutting wires of the invention are generally of substantially the same cross-sectional dimensions as are the electrosurgical cutting wires of the prior art. If they are circular in cross-section they will generally comprise Wire s have a diameter of from about 0.010 inch to about 0.100 inch. Thus, the electrosurgical electrodes of the invention can have equal strength and structural integrity as do the electrodes of the prior art. Yet, due to the presence of the sheath 22 and the slit 24, cutting and coagulation are much more controllable and adjacent tissue damage is greatly reduced.

Industrial Applicability

The present invention provides electrosurgical electrodes 10,110,210,310,410,510,610 with which surgical procedures can be carried out with reduced damage to adjacent tissue.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. In an electrosurgical electrode having an electrical conductor with a lateral surface and a longitudinal axis, the conductor being responsive to an electrical signal to direct a current to and perform a surgical function upon body tissue of a patient, an improvement comprising:
   a dielectric sheath surrounding said conductor and in surface contact with said conductor along the longitudinal axis, portions of the sheath defining a slit and limiting exposure of the lateral surface of the conductor to a particular area within the slit.

2. An electrosurgical electrode as set forth in claim 1, wherein said sheath includes a coating of dielectric material in contact with the lateral surface of the conductor.

3. An electrosurgical electrode as set forth in claim 2, wherein the dielectric material has characteristics providing the coating with a non-stick surface to minimize adhesion of the tissue to the electrode.

4. An electrosurgical electrode as set forth in claim 1, wherein said slit is coextensive with the particular area.

5. An electrosurgical electrode as set forth in claim 1, wherein said slit extends beyond said particular area and the electrode further comprises:
   an insulating sleeve disposed about said sheath in position to restrict the size of the particular area exposed through the slit and the sheath.

6. An electrosurgical electrode as set forth in claim 5, wherein the particular area has a length and a width and said insulating sleeve is slidable about the sheath to allow adjustment of the length of the particular area of the conductor.

7. An electrosurgical electrode as set forth in claim 1, wherein said slit is defined longitudinally along the sheath.

8. In an electrosurgical electrode having an electrical conductor with a lateral surface and a longitudinal axis, the conductor transmitting a radio frequency electrical signal which sparks to and performs a surgical function upon body tissue of a patient and is received by a receiver which is in conductive contact with the patient, an improvement comprising:
   a dielectric sheath surrounding said conductor along the longitudinal axis in a region where the surgical function is to be performed, the sheath having a slit extending therealong and exposing only a portion of the lateral surface of the conductor; and
   an insulating sleeve disposed about said sheath in position to restrict the area of the conductor exposed through the sheath.

9. An electrosurgical electrode as set forth in claim 8 wherein said insulating sleeve is slidable on said sheath to adjust the exposure of the lateral surface of the conductor.

10. In an electrosurgical electrode having an electrical conductor with a lateral surface and a longitudinal axis, the conductor transmitting a radio frequency electrical signal which sparks to and performs a surgical function upon body tissue of a patient and is received by a receiver which is in conductive contact with the patient, an improvement comprising:
    a dielectric sheath surrounding said conductor along the longitudinal axis in a region where the surgical function is to be performed, the sheath having a slit extending therealong and exposing only a portion of the lateral surface of the conductor; and
    an insulating sleeve disposed about and movable on said sheath and having a longitudinal window extending therethrough said insulating sleeve providing an aperture defined by at least portion of said window and by at least an area of said slit for selectively exposing a desired area of the conductor.

11. An electrosurgical device adapted to be disposed in proximity to tissue of a patient and to introduce to the tissue an electrical signal for performing a surgical function on the tissue, the intensity of the surgical function being dependent upon the current density of the electrical signal passing through the tissue, the device including:
   a supporting shaft;
   a conductor carried by the shaft and extending along a longitudinal axis, the conductor having a lateral surface;
   means slidable on and in surface contact with the conductor for adjusting the density of the current being introduced from the conductor to the tissue in order to selectively control the intensity of the surgical function being performed on the tissue;
   a sheath included in the adjusting means and surrounding the conductor in proximity to the tissue; and
   portions of the sheath defining a slit extending through the sheath and exposing at least a limited area of the lateral surface of the conductor, the size of the limited area being inversely proportional to the density of the current being introduced by the conductor to the tissue.

12. The device recited in claim 11 wherein the portions of the sheath defining the slit extend longitudinally of the axis of the conductor and define the entire limited area of the conductor.

13. The device recited in claim 11 further comprising:
   a sleeve disposed in movable relationship with the sheath;
   portions of the sleeve defining a window extending over the slit, the sleeve portions at least partially covering the slit; whereby
   the exposed limited area of the conductor is defined by both the portions of the sheath and the portions of the sleeve.

14. The device recited in claim 13 wherein the sleeve is slidable relative to the sheath to vary the size of the exposed limited area of the conductor.

15. The device recited in claim 13 wherein the sleeve is rotatable relative to the sheath to vary the size of the exposed limited area of the conductor.

16. The apparatus recited in claim 11 wherein:
   the supporting shaft extends between a proximal end and a distal end of the device;
   the conductor is bent from the shaft so that the longitudinal axis of the conductor is transverse to the shaft; and
   the shaft is disposed so that the portions of the sheath defining the slit are disposed in a facing relationship with the proximal end of the shaft.

17. An electrosurgical device adapted to be disposed in proximity to tissue of a patient and to introduce to the tissue an electrical signal for performing a surgical function on the tissue, the intensity of the surgical function being dependent upon the current density of the electrical signal passing through the tissue, the device including:
   a supporting shaft;
   a conductor carried by the shaft and extending along a longitudinal axis, the conductor having a lateral surface;
   means slidable on and in surface contact with the conductor for adjusting the density of the current being introduced from the conductor to the tissue in order to selectively control the intensity of the surgical function being performed on the tissue; and
   means disposed between the shaft and the conductor for moving the conductor radially of the shaft into proximity to the tissue.

18. The device recited in claim 17 wherein the moving means comprises a balloon having an cuter surface disposed in contact with the conductor, the balloon being inflatable to move the conductor radially outwardly of the shaft.

19. An electrosurgical electrode having a limited exposed area and being adapted to introduce an electrical signal to and perform a surgical function on, the tissue of a patient, the intensity of the surgical function being dependent on the size of the limited exposure area, the electrode comprising;
   a conductor having an elongate configuration and an cuter surface;
   insulating means disposed on the cuter surface of the conductor for inhibiting passage of the electrical signal from the conductor to the tissue;
   portions of the insulating means defining a slit having a size at least as large as the limited exposed area; whereby
   the size of the slit controls the intensity of the electrical signal passing from the limited exposed area of the conductor to the tissue to perform the surgical function.

20. The electrode recited in claim 19 wherein:
   the conductor includes a blade having at least two major surfaces and a lateral surface extending around the blade between the two major surfaces;
   the insulating means includes a coating disposed on each of the major surfaces of the blade; and
   the slit being defined to expose at least a portion of the lateral surface of the blade.

21. The electrosurgical electrode recited in claim 19 wherein the conductor is an active conductor in a bipolar electrode, and the electrosurgical electrode further comprises:
   a return conductor disposed in juxtaposition to the active electrode; and
   the insulating means is disposed on the active electrode with the portions of the insulating means defining the slit in facing relationship with the return conductor.

* * * * *

UNITED STATES PATENT AND TRADEMARK OFFICE
CERTIFICATE OF CORRECTION

PATENT NO. : 5,080,660
DATED : January 14, 1992
INVENTOR(S) : Terrence J. Buelna It is certified that error appears in the above—identified patent and that said Letters Patent is hereby corrected as shown below:

Col. 1, line 65 after the word "occur" delete the word "it" and add the phrase -- as a consequence, the tissue --

Col. 2, line 10 before the word "Radio" insert the word --A--.

Col. 2, line 15 after the word "being" add the word -- cut --.

Col. 2, line 17 after the word "case" delete the word "the".

Col. 2, line 18 after the word "the" (first occurance) add the phrase --active electrode or --.

Col. 2, line 32 after the word "carried" delete the word "cut" and add the word -- out --.

Col. 5, line 6 delete the first word of the sentence "sleeve s" and add the word -- sleeves --.

Col. 5, line 39 delete the words "Wire s have" and add the words -- wires having --.

Signed and Sealed this

Fourteenth Day of September, 1993

Attest:

BRUCE LEHMAN

*Attesting Officer*   *Commissioner of Patents and Trademarks*